(12) United States Patent
Wu

(10) Patent No.: US 6,840,892 B1
(45) Date of Patent: Jan. 11, 2005

(54) RECUPERATING MACHINE

(75) Inventor: Mu-Chuan Wu, Tainan Hsien (TW)

(73) Assignee: Tonic Fitness Technology, Inc., Tainan Hsien (TW)

( * ) Notice: Subject to any disclaimer, the term of this patent is extended or adjusted under 35 U.S.C. 154(b) by 95 days.

(21) Appl. No.: 10/225,151

(22) Filed: Aug. 22, 2002

(51) Int. Cl.[7] .............................................. A63B 71/00
(52) U.S. Cl. ........................................... 482/51; 482/62
(58) Field of Search ............................. 482/51, 57, 62, 482/904, 4–9

(56) References Cited

U.S. PATENT DOCUMENTS

| | | | | |
|---|---|---|---|---|
| 4,402,502 A | * | 9/1983 | Peters | 61/36 |
| 4,586,495 A | * | 5/1986 | Petrofsky | 602/2 |
| 4,586,510 A | * | 5/1986 | Glaser et al. | 607/48 |
| 4,824,132 A | * | 4/1989 | Moore | 280/304.1 |
| 4,846,156 A | * | 7/1989 | Kopnicky | 601/36 |
| 4,902,001 A | * | 2/1990 | Balbo | 482/62 |
| 4,947,836 A | * | 8/1990 | Laenger et al. | 607/48 |
| 5,980,431 A | * | 11/1999 | Miller, Jr. | 482/57 |
| 6,036,623 A | * | 3/2000 | Mitchell | 482/57 |
| 6,066,075 A | * | 5/2000 | Poulton | 482/8 |

* cited by examiner

*Primary Examiner*—Nicholas D. Lucchesi
*Assistant Examiner*—Tam Nguyen
(74) *Attorney, Agent, or Firm*—Bacon & Thomas

(57) ABSTRACT

A recuperating machine includes a bottom base and a machine body. The machine body has a frame in the interior, and a pair of grips and a pair of pedals combined on the frame in such way that the grips can be rotated manually and the pedals not moving only for the feet of a user to step on or the pedals possible to be rotated but the grips not moving only for holding by means of a one-way bearing. So a user can select two modes of exercising by moving the hands only or by moving the feet only. Depending on the body condition of the user. Further the frame is pivotally connected with the front end of the bottom base for adjusting its inclining angles to suit to the height of a user sitting on a chair or a wheelchair.

3 Claims, 3 Drawing Sheets

RECUPERATING MACHINE

BACKGROUND OF THE INVENTION

This invention relates to a recuperating machine, particularly to one provided with different modes for a user to select for exercise, having advantages of selectability increased and recuperating effect enhanced.

A conventional recuperating machine is for a patient such as one suffering a stroke to exercise feet and legs so as to recover walking ability as soon as possible, and it generally includes an almost vertical machine body, a pair of manual grips extending sidewise from two sides of an upper end of the machine body, and a pedal rod with two pedals. The manual grips and the pedal rod are connected with a belt. Then a user is moved to the front location of the recuperating machine, made to grip the manual grips and place two feet on the pedals. In this position, the user moves and let the manual grips swing around to force the belt rotate the pedal rod synchronously so that the user's feet may receive up-and-down movement of the two pedals to train and strengthen the muscle of the two feet and legs.

However, the conventional recuperating machine has been found to have some disadvantages in its structure and design. As the conventional recuperating machine utilizes manual grips for directly rotating the pedal rods and the pedals in a synchronous way, its exercising method adopts a mode of "both hands moving the two feet and legs", not the two feet directly pedaling the two pedals. Then this method cannot know how much the muscle of two feet and legs are strengthened. In addition, if the two hands of the user do not hold the grips and the two feet directly pedal the pedals, it can increase the strength of the two feet and legs. But as the manual grips and the pedals are moved synchronously, the grips are also moved continually in the air during movement of the feet. Then the grips may collide with a person passing by the recuperating machine in case of the person being careless. Moreover, as the hands of the user does not hold the grips, with the feet and legs stepping on the pedals, the user sitting on the a chair or a wheelchair may become unstable and sway around. Then this kind of recuperating machine may suit for a patient having no force in the muscle of the feet and legs, but having force in the hands and arms. After a period of time of exercising and training, the conventional recuperating machine may not be suitable, when the patient has obtained some strength in the feet and legs.

SUMMARY OF THE INVENTION

The purpose of the invention is to offer a new kind of recuperating machine provided with different modes for exercise and training so that a user may select to use according to the physical condition of his/her own body, having advantages of selectability increased and recuperating effect enhanced.

The recuperating machine in the invention includes a bottom base, a machine body provided to extend upright from the front end of the machine body. The bottom body has a pair of positioning rods respectively provided at two sides of an intermediate portion and an outer end, possible to expand and shrink, and a positioning plate provided between the two pairs of the positioning rods.

The machine body has a frame having a lower end pivotally connected to a front end of the bottom base and vertical but a little inclining rearward. A pair of manual grips are connected with two ends of a grip supporting shaft provided near an upper end of the frame. A pair of pedals are connected to two ends of two pedal rods connected with two ends of a pedal supporting shaft provided rotatably on a lower end of the frame. Further a force-resisting device is provided on an intermediate portion of the frame by means of a resisting-force supporting shaft. Then the grip supporting shaft, the pedal supporting shaft and the resisting-force device respectively have a belt wheel and rotate with each other by means of belts so that the grips may move the pedal rods and the force-resisting device. Further a one-way bearing is provided in the bell wheel of the pedal-supporting shaft.

Thus, a user of the recuperating machine can select one mode of holding the grips with the hands and the feet only stepping on the pedals but not pedaling and rotated by the grips moved by the hands. Or a user can select another mode of pedaling the pedals with the feet but with the hands only holding the grips, which does not rotate owing to the one-way bearing. The first mode is suitable for a patient having no strength on the feet, and the second mode is rather suitable for a patient having some strength on the feet for recuperating.

BRIEF DESCRIPTION OF DRAWINGS

This invention will be better understood by referring to the accompanying drawings, wherein.

DETAILED DESPRIPTION OF THE PREFERRED EMBODIMENT

Figure 1:
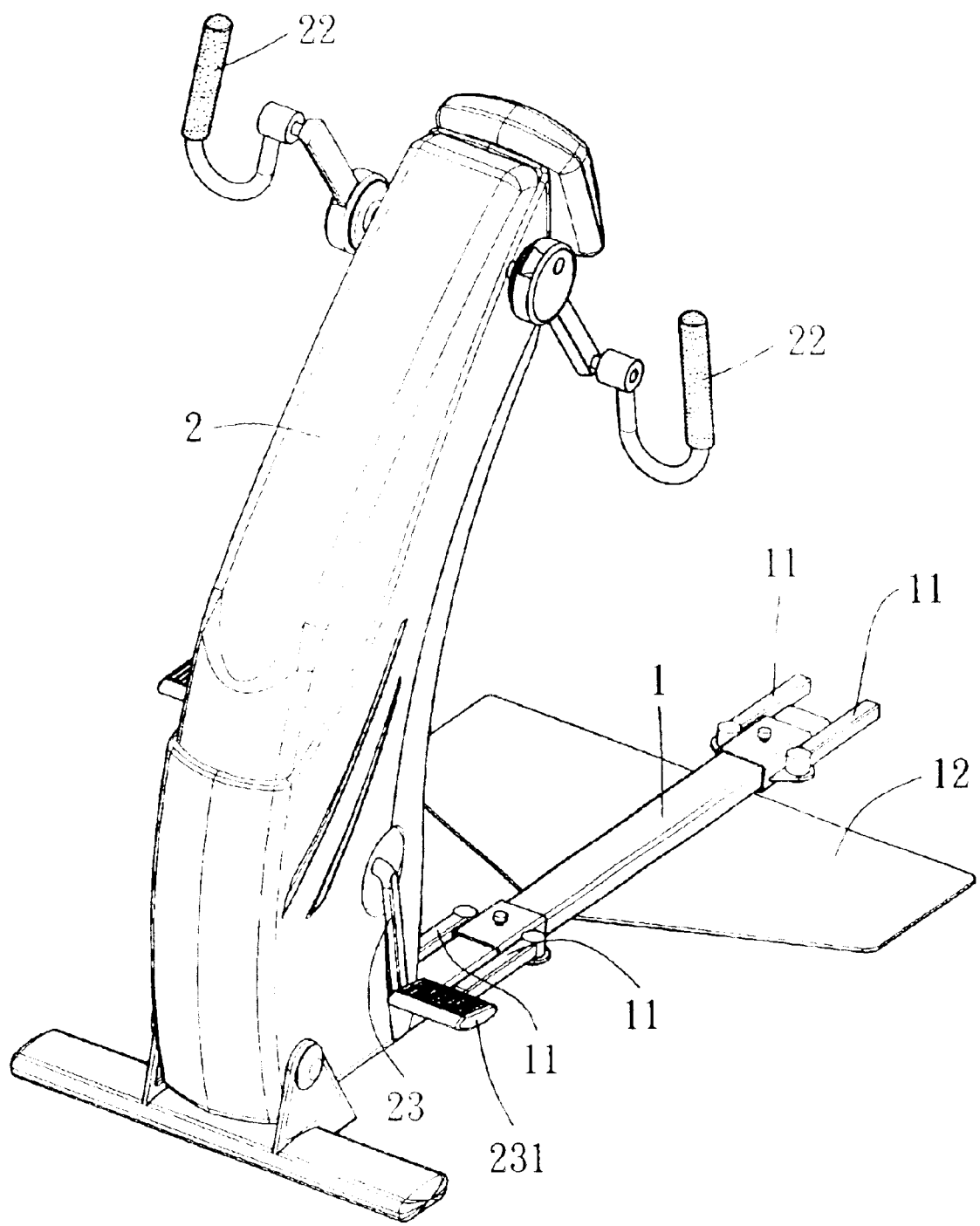
FIG. 1 is a perspective view of a recuperating machine in the present invention.

A preferred embodiment of a recuperating machine in the present invention, as shown in FIG. 1, includes a bottom base 1 and a machine body 2 extending up from a front end of the bottom base 1.

The bottom base 1 has a pair of positioning rods 11 provided respectively on two sides of an intermediate portion and on an outer end and extensible outward and shrinkable inward, and a multi-side positioning plate 12 provided between the two pairs of positioning rods 11.

Figure 2:
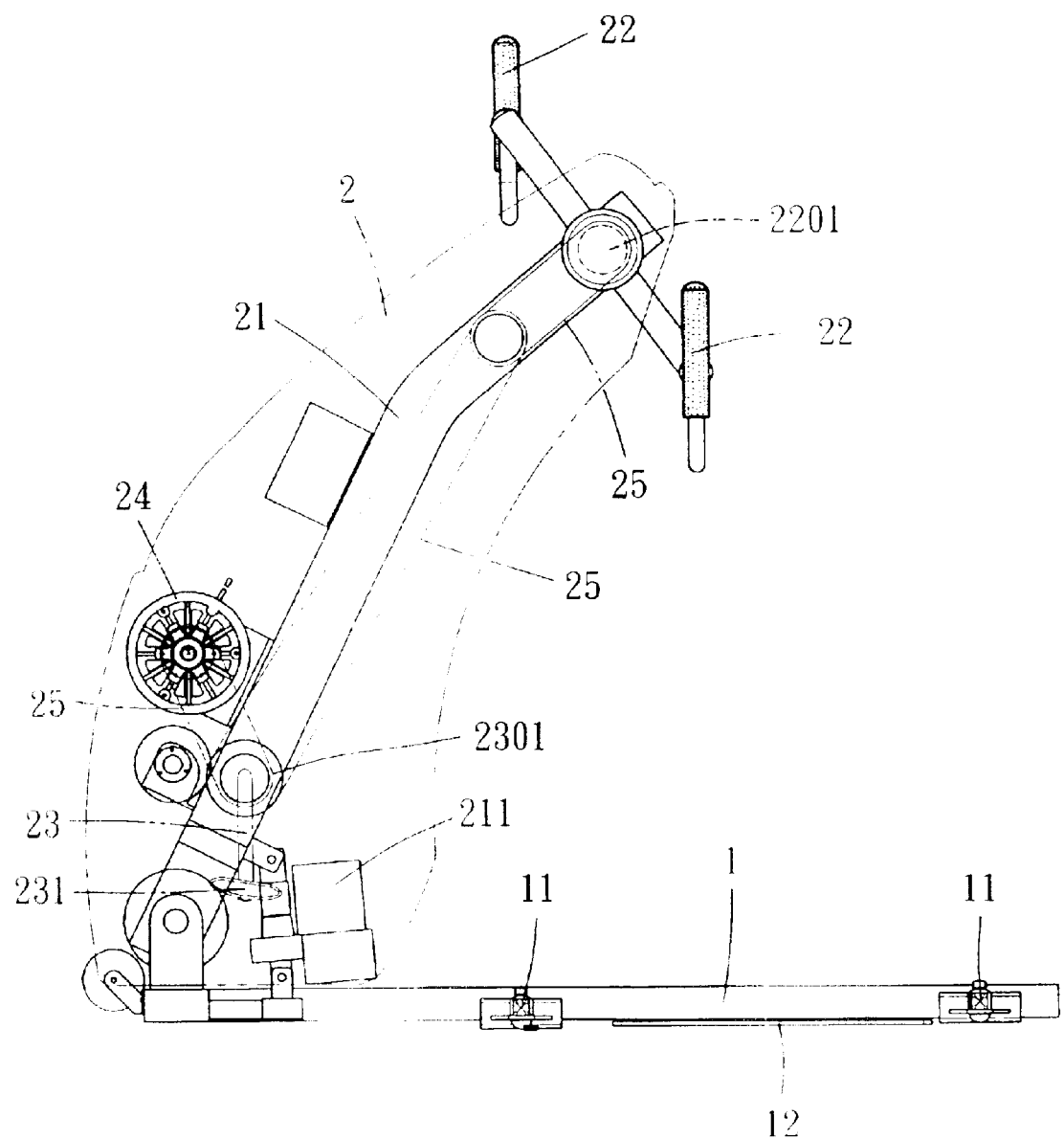
FIG. 2 is a side view of the inside structure of the recuperating machine in the present invention; and, FIG. 3 is a front view of the inside structure of the recuperating machine in the present invention.
Figure 3:
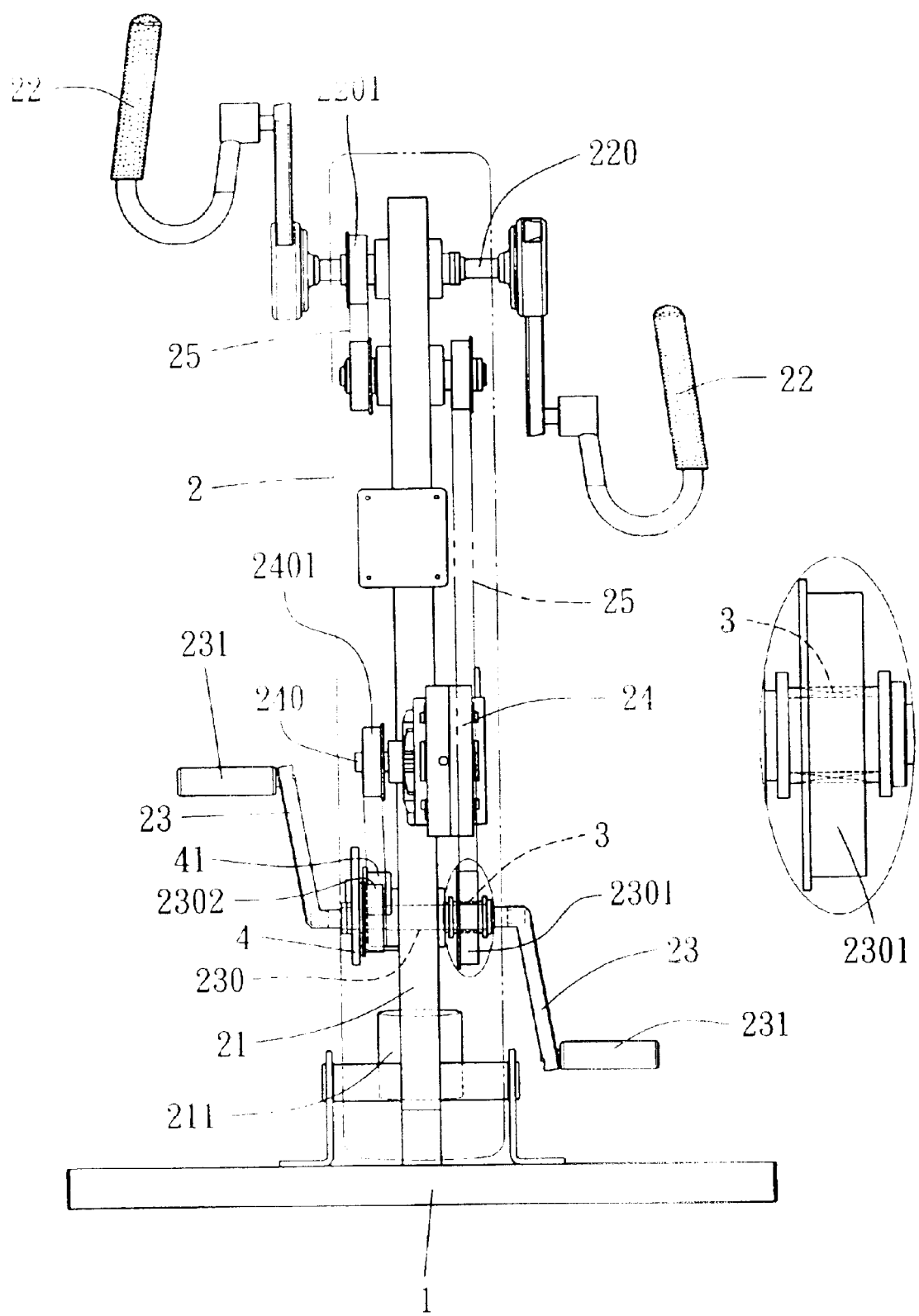

The machine body 2 is positioned at the front end of the bottom base 1, having a frame 21 provided in its interior, positioned vertical but a little inclining rearward. The frame 21, as shown in FIGS. 2 and 3, has its lower end connected with the front end of the bottom base 1, and a motor 211 is positioned between the bottom of the frame 21 and the bottom base 1 for adjusting the inclining angle of the frame 21. Then a grip supporting shaft 220 is provided near the top end of the frame 21, and a pair of manual grips 22 is fixed with the grip supporting shaft 220, extending to two outer sides of the machine body 2 and rotatable manually. Further, a pedal-supporting shaft 230 is provided near the lower end of the frame 21, and a pair of pedal rods 23 extends to two opposite sides of the machine body 2 from two ends of the pedal-supporting shaft 230, with a pedal 231 respectively connected with the outer ends of each pedal rod 23.

Next, a force-resisting device 24 is provided on a resisting-force supporting shaft 240 fixed on an intermediate portion of the frame 21. The grip support shaft 220 and the resisting force supporting shaft 240 are respectively have a belt wheel 2201, 2401, and the pedal-supporting shaft 230 is connected with the grip supporting shaft 220 and the resisting force supporting shaft 240 at the same time. A first belt wheel 2301 and a second belt wheel 2302 are respectively fixed at two ends of the pedal supporting shaft 230, and the first belt wheel 2301 is rotated together with the belt wheel 2401 of the resisting-force supporting shaft 240 as shown in FIG. 3. A one-way bearing 3 is further provided between the pedal supporting shaft 230 and the first belt wheel 2301, and a gear 4 is provided on one side of the pedal-supporting shaft 230 and rotates synchronously with the same shaft 230 as shown in FIG. 3. Then the gear 4 is connected to and rotates an encoder 41 so that the encoder 41 may be connected electrically with an electrical stimulating device (not shown) independent of the machine body 2.

After the recuperating machine is assembled together as described above, a patient sitting on a wheelchair or a chair is moved onto the positioning plate 12, with the positioning rods 11 spread out and blocking the front and the rear end of the chair 5 to stabilize the chair 5. Then the inclination angle of the frame 21 is adjusted by starting the motor 211, positioning properly the grips 22 and the pedals 231 at a suitable height for the user. Now the patient can place attaching pieces of the electrical stimulating device on points for acupuncture or the circulation system of blood on the feet and legs, with the two hands holding the two grips 22 and the two feed stepping on the pedals 231.

Then the user selects an operating mode for recuperating, for example, at first, a first mode of exercising with "two hands and arms moving the two feet and legs". This first mode can be considered to be warming exercise and comparatively proper for a beginner (one who has the feet and legs with no strength, unable to pedal), with two hands holding the grips 22 and two feet stepping on the pedals 231. Then the user swings around the grips 22 with the hands, forcing the belt wheels 2201, 2301, 2302 and 2401 rotate so as to let the belts 25 transmitting the force-resisting device 24 and the pedal rods 23 to rotate so that the pedal rods 23 and the pedals 231 synchronously rotate clockwise to produce a stepping resisting force. In this way, the feet and legs of the user produce pedaling movement.

A second mode of operating the recuperating machine is "pedaling directly with two feet and legs", i.e. a user can proceed with this mode for exercising after the above-mentioned first mode, and one who has comparative feet strength also can directly use this second mode. Then the user firmly holds the two grips 22, but needs not to swing them around and only for supporting and balancing, with the feet stepping on the pedal 231 and pedaling them as though pedaling a bicycle. In this condition, as the one-way bearing 3 only rotates in one direction, and the pedal supporting shaft 230 rotates as a main force, so the pedal supporting shaft 230 does not produce interacting action against the one-way bearing 3 so that the first belt wheel 2301 cannot rotate, permitting the two grips 22 continue to keep immovable, letting the two hands of the user only holding them without moving. But the second belt wheel 2302 still rotates the force-resisting device 24, so this second mode is completely performed by direct force of the feet of the user, with the two hands doing supporting and balancing only.

A third mode for operating the recuperating machine is "synchronous movement of the hands and arms and the feet and legs", and a user holds the grips 22 with two hands and stepping on the pedals 231 with the feet. Then the user uses the force of the hands and the feet simultaneously in swinging around the grips 22 and pedaling the pedals 231, making synchronous exercise with the hands and the feet.

It is to be emphasized that the pedal-supporting shaft 230 is always kept rotating, no matter which mode of operating the recuperating machine is used by. Further, the gear 4 may rotate the encoder 41 during the synchronous movement of the pedal supporting shaft 230, letting the encoder 41 transmit the data of the rotating condition of the gear 4 to the electrical stimulating device independent of the machine body 2. Then the electrical stimulating device reads the data to be aware of the feet and the legs extending or shrinking, and then transmits proper current to the attaching pieces on the feet and legs of the user, enhancing effectiveness of stimulating the points for acupuncture or the circulation system of blood for strengthening recuperating.

It is preferably noticed that the grips 22 does not move owning to the one-way bearing 3, so there may happen no accident of colliding with a person passing nearby.

While the preferred embodiment of the invention has been described above, it will be recognized and understood that various modifications may be made therein and the appended claims are intended to cover all such modifications that may fall within the spirit and scope of the invention.

I claim:

1. A recuperating machine comprising:

a bottom base:

a machine body having a frame slightly inclining rearwards to said bottom base, said frame pivotally connected with a front end of said bottom base;

a grip supporting shaft provided near an upper end of said frame:

a pair of grips fixed with two ends of said grip supporting shaft and respectively extending to two opposite sides of said machine body, capable of being manually swung around;

a pedal-supporting shaft fixed near a bottom end of said frame;

a pair of pedal rods respectively fixed at two ends of said pedal supporting shaft and extending to two opposite sides of said machine body;

a pedal connected respectively with an outer end of each of said pedal rods;

a force-resisting rod provided on said frame;

a force-resisting device fixed on an intermediate portion of said force-resisting rod;

a belt wheel respectively provided on said grip supporting shaft, said pedal supporting shaft rotating together with said grip supporting shaft and said force-resisting rod;

a first belt wheel and a second belt wheel respectively provided on two ends of said pedal supporting shaft, said first belt wheel and said belt wheel of said grip supporting shaft connected together by a belt, said second belt wheel rotating together with said belt wheel of said force-resisting rod;

a one-way bearing provided between said pedal-supporting shaft and said first belt wheel; and a first mode of manual rotation of said grips is selectable by a user by holding and rotating said grips with two hands and with two feet only stepping on said pedals if the user does not have strength on the feet and legs, a second mode of pedaling said pedals is selected by a user with the feet and hands only holding but not rotating said grips if the user has some strength on the feet so as to directly exercise the feet for recuperating.

2. The recuperating machine as claimed in claim 1, further comprising a motor provided between the lower end of said frame and said bottom base for adjusting the inclining angle of said frame.

3. The recuperating machine as claimed in claim 1, further comprising a gear provided on a left side of said pedal supporting shaft, and an encoder is provided to be rotated by said gear, said encoder connected electrically with an electrical stimulating device provided independent of said machine body, said electrical stimulating device receiving data from said encoder rotating together with said gear which is rotated together with said pedal supporting shaft, said electrical stimulating device transmitting proper current according to the data indicating the extended or retreated condition of the user's feet and legs so as to stimulate points of acupuncture and user's blood circulation.

* * * * *